US011950934B1

(12) United States Patent
Elmallah et al.

(10) Patent No.: US 11,950,934 B1
(45) Date of Patent: Apr. 9, 2024

(54) INPUT BOOSTING FOR CHOPPED NEURAL RECORDING SYSTEMS

(71) Applicant: Verily Life Sciences LLC, South San Francisco, CA (US)

(72) Inventors: Ahmed Elmallah, Urbana, IL (US); James Salvia, Belmont, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 56 days.

(21) Appl. No.: 16/946,342

(22) Filed: Jun. 17, 2020

Related U.S. Application Data

(60) Provisional application No. 62/864,808, filed on Jun. 21, 2019.

(51) Int. Cl.
*A61B 5/00* (2006.01)
*A61B 5/30* (2021.01)
*H03F 3/38* (2006.01)

(52) U.S. Cl.
CPC .......... *A61B 5/7225* (2013.01); *A61B 5/0048* (2013.01); *A61B 5/30* (2021.01); *A61B 5/486* (2013.01); *H03F 3/38* (2013.01); *H03F 2200/271* (2013.01)

(58) Field of Classification Search
CPC ....... A61B 5/7225; A61B 5/0048; A61B 5/30; A61B 5/486; H03F 3/38; H03F 2200/71
See application file for complete search history.

(56) References Cited

U.S. PATENT DOCUMENTS

| 7,385,443 | B1* | 6/2008 | Denison | A61B 5/7217 330/10 |
| 9,757,071 | B1* | 9/2017 | Fazi, Jr. | A61B 5/339 |
| 10,958,226 | B2* | 3/2021 | Daniels | H03F 1/342 |
| 2012/0161994 | A1* | 6/2012 | Quiquempoix | H03F 3/005 330/69 |

(Continued)

FOREIGN PATENT DOCUMENTS

CN 105651452 A * 6/2016

OTHER PUBLICATIONS

Machine Translation of CN105651452A, provided by Google Patents, Nov. 20, 2023. (Year: 2016).*

(Continued)

*Primary Examiner* — Michael R Bloch
(74) *Attorney, Agent, or Firm* — Kilpatrick Townsend & Stockton LLP (57) ABSTRACT

Described herein is a front-end for a neural recording system that boosts input impedance of the front-end circuit. The front-end includes an amplifier and two choppers. A first input terminal of the first chopper may be coupled to a first output terminal from one or more signal sensors. A first input terminal of the second chopper may be coupled to a second output terminal from the signal sensors. A second input terminal of the first chopper may be coupled to a first output terminal of a feedback subsystem. A second input terminal of the second chopper may be coupled to a second output terminal of the feedback subsystem. The output terminals of each chopper may each be coupled to a different capacitor such that after switching, the voltage of each capacitor remains substantially the same, improving the input impedance of the circuit.

14 Claims, 5 Drawing Sheets

(56) References Cited

U.S. PATENT DOCUMENTS

| | | | |
|---|---|---|---|
| 2013/0113553 A1* | 5/2013 | Hsieh | H03F 3/387 330/9 |
| 2016/0262703 A1 | 9/2016 | Maccallum | |
| 2017/0230019 A1 | 8/2017 | Chandrakumar et al. | |
| 2019/0150777 A1* | 5/2019 | Guo | A61B 5/30 |

OTHER PUBLICATIONS

Bharucha et al., "A survey of neural front end amplifiers and their requirements toward practical neural interfaces", Journal of Low Power Electronics and Applications 4.4 (2014): 268-291.

Chandrakumar et al., "A High Dynamic-Range Neural Recording Chopper Amplifier for Simultaneous Neural Recording and Stimulation", IEEE Journal of Solid-State Circuits, vol. 52. No. 3, Mar. 2017, pp. 645-656.

Chandrakumar et al., "27.1 A 2.8 µW 80mV pp-linear-input-range 1.6 GΩ-input impedance bio-signal chopper amplifier tolerant to common-mode interference up to 650mV pp", 2017 IEEE International Solid-State Circuits Conference (ISSCC). IEEE, 2017.

Chandrakumar , "Implantable Neural Recording Front-Ends for Closed-Loop Neuromodulation Systems", UCLA, 2017.

Hu et al., "A low power 100MΩ CMOS front-end transimpedance amplifier for biosensing applications", 2010 53rd IEEE International Midwest Symposium on Circuits and Systems. IEEE, 2010.

Kosari et al., "A 0.5 V 68 nW ECG Monitoring analog front-end for arrhythmia diagnosis", Journal of Low Power Electronics and Applications 8.3 (2018): 27.

Liu et al., "Design of a low-noise, high power efficiency neural recording front-end with an integrated real-time compressed sensing unit", 2015 IEEE International Symposium on Circuits and Systems (ISCAS). IEEE, 2015, 2996-2999.

Liu et al., "Neural Recording Front-End Design", Brain-Machine Interface. Springer, Cham, 2018. 17-68.

Muller et al., "A miniaturized 64-channel 225µW wireless electrocorticographic neural sensor", 2014 IEEE International Solid-State Circuits Conference Digest of Technical Papers (ISSCC). IEEE, 2014.

Ng et al., "Implantable neurotechnologies: a review of integrated circuit neural amplifiers", Medical & biological engineering & computing 54.1 (2016): 45-62.

Regalia et al., "A low-noise, modular, and versatile analog front-end intended for processing in vitro neuronal signals detected by microelectrode arrays", Computational intelligence and neuroscience 2015 (2015).

Yang et al., "A high input impedance low-noise instrumentaion amplifier with JFET input", 2013 IEEE 56th International Midwest Symposium on Circuits and Systems (MWSCAS). IEEE, 2013.

Zhou et al., "A high input impedance low noise integrated front-end amplifier for neural monitoring", IEEE transactions on biomedical circuits and systems 10.6 (2016): 1079-1086.

* cited by examiner

INPUT BOOSTING FOR CHOPPED NEURAL RECORDING SYSTEMS

CROSS-REFERENCE TO RELATED APPLICATIONS

This application claims priority to U.S. Provisional Patent Application No. 62/864,808, filed on Jun. 21, 2019, titled "Input Boosting for Chopped Neural Recording Systems," the contents of which are hereby incorporated by reference in their entirety.

FIELD

The present application generally relates to neural signal recording systems and more specifically relates to input boosting for chopped neural recording systems.

BACKGROUND

High precision electronics having one or more choppers in the front-end circuitry may suffer from low input impedance due to the switching of the choppers. A coupling capacitor that couples the chopper to an amplifier may have to be charged by the input source because of the changes in voltage caused by the switching of the choppers. The charging of the coupling capacitors may lower the circuit input impedance. The higher the frequency at which the choppers switch, the lower the circuit input impedance becomes; and low input impedance may limit the frequency range detectable by the circuit.

SUMMARY

One general aspect includes a front-end for a neural recording system, the front-end may include two choppers. A first input terminal of the first chopper may be electrically coupled to a first output terminal from a neural sensor electrode. A second input terminal of the first chopper may be configured to be electrically coupled to a first output terminal of a feedback subsystem. A first input terminal of the second chopper may be electrically coupled to a second output terminal from the neural sensor electrode. A second input terminal of the second chopper may be electrically coupled to a second output terminal of the feedback subsystem. The front-end may further include multiple capacitors and an amplifier. A first capacitor may be coupled between a first output terminal of the first chopper and a first (e.g., positive) input terminal of the amplifier. A second capacitor may be coupled between a second output terminal of the first chopper and a second (e.g., negative) input terminal of the amplifier. A third capacitor may be coupled between a first output terminal of the second chopper and the second input terminal of the amplifier. A fourth capacitor may be coupled between a second output terminal of the second chopper and the first input terminal of the amplifier.

Implementations may include one or more of the following features. In some embodiments, a first coupling capacitor may be electrically coupled between the first input terminal of the first chopper and the first output terminal of the sensor electrode and a second coupling capacitor may be electrically coupled between the first input terminal of the second chopper and the second output terminal of the sensor electrode. In some embodiments, the amplifier may include an output terminal that is electrically coupled to an input terminal of the feedback subsystem. In some embodiments, the front-end may include the sensor electrode that measures a response signal from a nerve of a patient. Implementations of the described techniques may include hardware, a method or process, or computer software on a computer-accessible medium.

Another general aspect includes a neural recording system. The neural recording system may include a sensor electrode that measures a response signal from a nerve of a patient. The neural recording system may also include a feedback subsystem that generates a feedback signal to substantially match the response signal. The neural recording system may also include a chopping amplifier front-end. The chopping amplifier front-end may include a first chopper having two input terminals and two output terminals. The first input terminal of the first chopper may be coupled to a first output terminal of the sensor electrode. The second input terminal of the first chopper may be coupled to a first output terminal of the feedback subsystem. The chopping amplifier front-end may include a second chopper having two input terminals and two output terminals. The first input terminal of the second chopper may be coupled to a second output terminal of the sensor electrode. The second input terminal of the second chopper may be coupled to a second output terminal of the feedback subsystem. The chopping amplifier front-end may further include an amplifier having two input terminals and an output terminal. The first input terminal of the amplifier may be electrically coupled to a first output terminal of the first chopper and a first output terminal of the second chopper. The second input terminal of the amplifier may be electrically coupled to a second output terminal of the first chopper and a second output terminal of the second chopper. The output terminal of the amplifier may be electrically coupled to an input terminal of the feedback subsystem.

Implementations may also include one or more of the following features. In some embodiments, the neural recording system may include a recording subsystem electrically coupled to the feedback subsystem and configured to receive and record the response signal. In some embodiments, the feedback subsystem may include a control subsystem, where an input of the control subsystem is electrically coupled to the output terminal of the chopping amplifier front-end. In some embodiments, the neural recording system may include an output device, where an input terminal of the output device is electrically coupled to an output terminal of the control subsystem. In some embodiments, the neural recording system may include a stimulation subsystem that stimulates the patient to evoke the response signal from the nerve of the patient. In some embodiments, the neural recording system may further include first coupling capacitor electrically coupled between the first output terminal of the sensor electrode and the first input terminal of the first chopper and a second coupling capacitor electrically coupled between the second output terminal of the sensor electrode and the first input terminal of the second chopper. In some embodiments, the neural recording system may include several coupling capacitors. The coupling capacitors may include a first coupling capacitor electrically coupled between the first output terminal of the first chopper and the first input terminal of the amplifier, a second coupling capacitor electrically coupled between the second output terminal of the first chopper and the second input terminal of the amplifier, a third coupling capacitor electrically coupled between the first output terminal of the second chopper and the second input terminal of the amplifier, and a fourth coupling capacitor electrically coupled between the second output terminal of the second chopper and the first input terminal of the amplifier. Implementations of the described techniques may include hardware, a method or process, or computer software on a computer-accessible medium.

Another general aspect includes a method for receiving nerve response signals. The method may include configuring a first chopper and a second chopper of a front-end of a neural recording system to receive a response signal from a sensor electrode monitoring a nerve of a patient. The method may also include configuring the first chopper and the second chopper of the front-end of the neural recording system to receive a feedback signal from a feedback subsystem. The method may also include configuring the first chopper and the second chopper to chop the feedback signal and response signal to provide a response voltage value and a feedback voltage value. The method may also include configuring a first, second, third, and fourth coupling capacitor to receive one of the response voltage value or the feedback voltage value during a first phase of the first and second chopper and the other of the response voltage value or the feedback voltage value during a second phase of the first and second chopper such that each of the first, second, third, and fourth coupling capacitors see a substantially consistent voltage that does not change polarity during a neural recording session. The method may also include configuring a first input of an amplifier of the front-end of the neural recording system to receive a first error difference between the response signal and the feedback signal via at least two of the plurality of coupling capacitors. The method may also include configuring a second input of the amplifier of the front-end of the neural recording system to receive a second error difference between the response signal and the feedback signal via at least two of the plurality of coupling capacitors. The method may also include configuring the amplifier to amplify the difference between the first error difference and the second error difference to produce an amplified error signal. The method may also include configuring the feedback subsystem to receive the amplified error signal. The method may also include configuring the feedback subsystem to tune the feedback signal using the amplified error signal. Other embodiments of this aspect include corresponding computer systems, apparatus, and computer programs recorded on one or more computer storage devices, each configured to perform the actions of the methods.

Implementations may include one or more of the following features. In some embodiments, the feedback signal substantially matches the response signal. In some embodiments, the method may further include configuring a stimulation subsystem to stimulate the nerve of the patient. In some embodiments, the method may further include configuring a recording subsystem to record, in a database, the response signal of the nerve of the patient during the neural recording session. In some embodiments, the method may further include configuring an output device to display the response signal. In some embodiments, the method may further include configuring a user input device to receive parameter values for the neural recording session. Implementations of the described techniques may include hardware, a method or process, or computer software on a computer-accessible medium.

BRIEF DESCRIPTION OF THE DRAWINGS

A further understanding of the nature and advantages of various examples may be realized by reference to the following figures.

Unless otherwise indicated, elements using the same indicator number are the same elements between differing figures. Some elements may include multiple of the same elements, which are indicated by a letter following the indicator number

DETAILED DESCRIPTION

Examples of front-ends for a signal recording system are disclosed. Different examples of signal recording systems may include any high precision electronic circuit including, for example, a neural recording system. Neural recording systems measure and record brain activity of a patient or subject. This activity is specifically identified by measuring the electro-physiological responses of single neurons within the brain of the patient or subject. In some cases neural recording systems record the activity based on a stimulus applied to the patient or subject, while in some cases the activity of the nerve or brain without stimulus is captured and recorded. While a neural recording system is often discussed herein, the techniques disclosed are suitable for any signal recording system and/or any high precision electronics having a chopping amplifier in a circuit where boosted input impedance is desired. An example signal recording system is designed as a feedback system that includes several components. The components may include a front-end and a feedback subsystem. The front-end of the signal recording system may include a chopping amplifier circuit that may include two choppers and an amplifier. Response signals to the choppers are received from electrodes detecting signals, for example, from one or more nerves in a subject (e.g., test subject or patient).

In addition to the front-end, the signal recording system may include a feedback subsystem, which is designed to generate an output signal (i.e., feedback signal) that matches (as closely as possible) the response signals received from the electrodes. In addition to the response signals received from the electrodes, the input to the two choppers may also include the output of the feedback subsystem. The front-end circuitry may then determine any error between the output of the feedback subsystem and the response signals received from the electrodes. This error is output as an error signal, which is amplified by the amplifier. The amplified error signal may be provided to other components of the neural recording system. For example, the amplified error signal is provided to the feedback subsystem and used to tune the feedback signals to more closely match the response signals received from the electrodes. In this improved front-end, the configuration of the choppers keep the coupling capacitors between the output of the choppers and the input of the amplifier charged to substantially the same voltage at all times, boosting the input impedance.

Boosting the input impedance of the front-end has multiple benefits. First, when the input impedance is boosted, the frequencies at which the response signals from the electrodes can be detected is expanded to allow detection of lower frequency response signals. Second, the capacitors on the chip can be smaller, allowing for a smaller circuit footprint and reduced device size. Third, high input impedance can protect the tissue of the subject (e.g., patient) during a neural recording procedure.

As used herein, "coupled" means electrically coupled, directly or indirectly, when referring to electrical components. Electrically coupled means that electrical energy (e.g., current) may pass from one component to the coupled component, directly or indirectly. For example, when two components, such as a chopper and an amplifier, are coupled, the current flowing through the chopper may reach the amplifier directly or by flowing through another component, such as a coupling capacitor that is coupled between the chopper and the amplifier. "Coupled" may also mean mechanically coupled, directly or indirectly, when referring to physical components. Mechanically coupled means that the components are physically attached, directly or indirectly. For example, when two components, such as a sensor and a chopper, are mechanically coupled, the sensor may be directly attached to the chopper, or the sensor may be attached to the chopper via a third component, such as a coupling capacitor that is physically attached to the sensor on one side and physically attached to the chopper on the other side. Additionally, a physical connection may be any length of conductive material (e.g., a wire) that couples two or more components.

Figure 1:
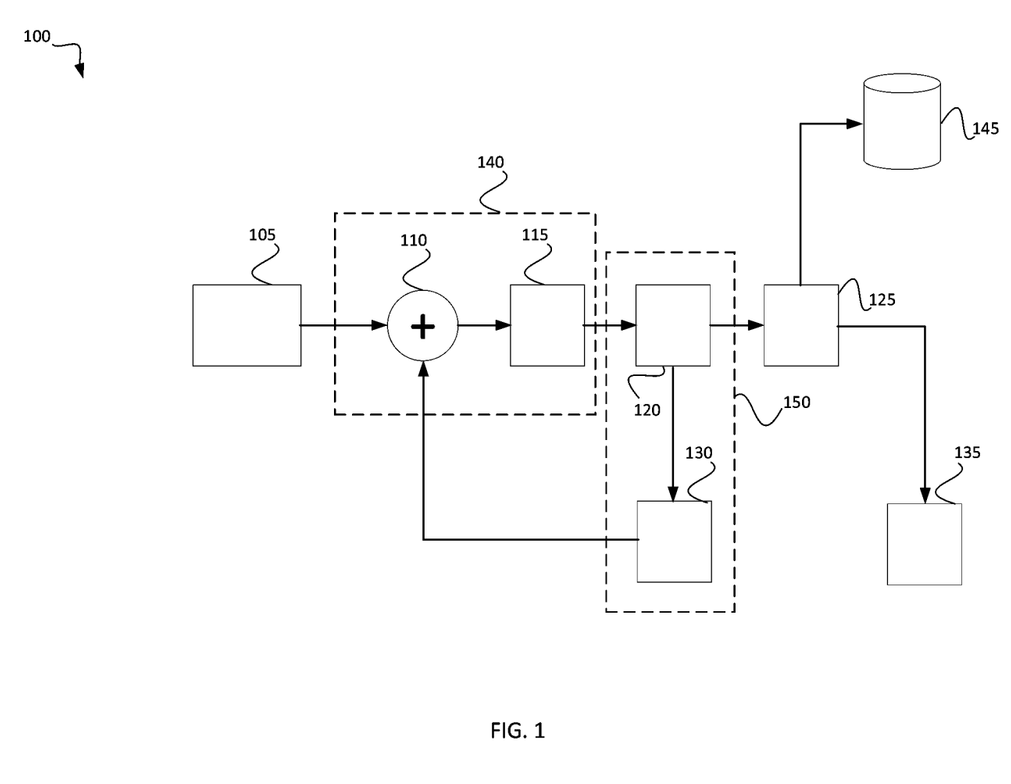
FIG. 1 illustrates a simplified diagram of a signal recording system, according to some embodiments.

FIG. 1 illustrates an example signal recording system 100. The signal recording system 100 may be, for example, a neural recording system. This example signal recording system 100 includes one or more sensor electrodes 105, chopping node 110, amplifier 115, control subsystem 120, recording subsystem 125, feedback actuator 130, I/O device 135, and digital storage medium 145. The chopping node 110 and amplifier 115 together form a chopping amplifier circuit 140. The control subsystem 120 and feedback actuator 130 together form the feedback subsystem 150. While specific nodes and subsystems are depicted within signal recording system 100, more or fewer components may be included without departing from the scope of this disclosure.

Figure 5:
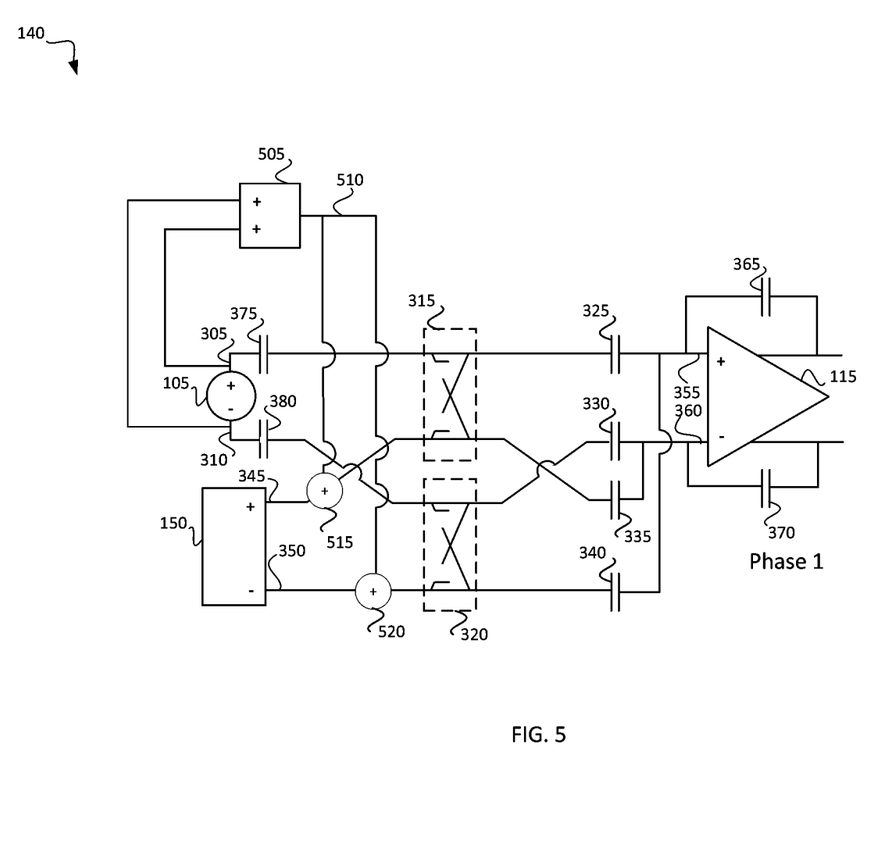
FIG. 5 illustrates a front-end of the signal recording system of FIG. 1 according to some embodiments.

Sensor electrodes 105 may be any suitable electrodes 105 that may be used to measure a response signal from a nerve of a subject or patient. In some embodiments, the sensor electrodes 105 may also provide a stimulation to the nerve of the patient that evokes the response signal. In some embodiments, stimulation may be provided by any other suitable means to the patient that evokes the response signal measured by the sensor electrodes 105. The subject may be, for example, a test subject, a human patient, an animal, or any other suitable subject that may output a response signal detectable by sensor electrodes 105, including electronic or mechanical systems. In some embodiments, for example, the sensor electrodes 105 may detect a response signal from a brain, a spinal cord, or any other nerves of the subject. The output from the sensor electrodes 105 has two components—a common mode component and a differential mode component. The impedance boosting discussed herein can be the common mode impedance, the differential mode impedance, or the full (i.e., common mode and differential mode) impedance. Boosting common mode impedance, differential mode impedance, or full impedance may be useful in various applications. As discussed further herein, the feedback system 150 can work on common mode impedance, differential mode impedance, or full impedance. For simplicity sake the discussion of FIGS. 1, 3A, and 3B focus on differential mode impedance boosting. However, common mode impedance boosting or full impedance boosting are also possible. FIG. 5 illustrates an example front-end for full impedance boosting. Common mode impedance boosting is also described with respect to FIG. 5.

Figure 3A:
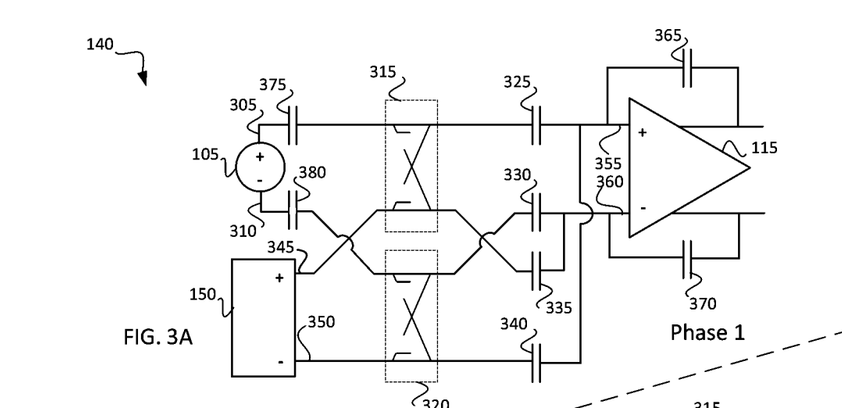
FIGS. 3A and 3B illustrate the two phases of a front-end of the signal recording system of FIG. 1, according to some embodiments.
Figure 3B:
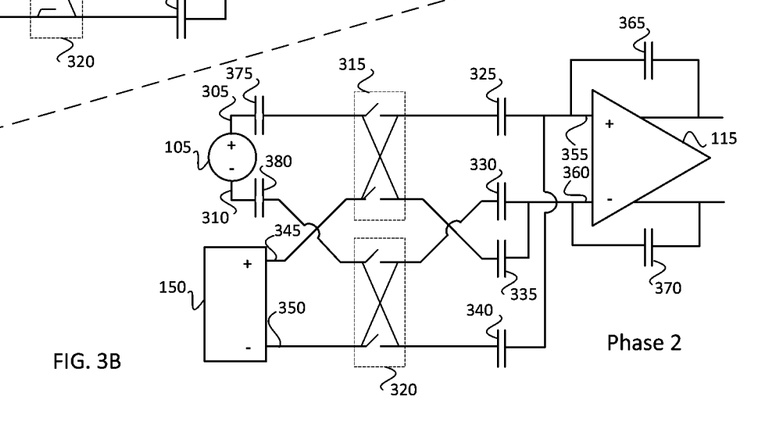

In this example, chopping node 110 includes components described in further detail below with respect to FIGS. 3A and 3B. The input terminals of chopping node 110 receive the output of sensor electrodes 105 as well as the output of feedback subsystem 150. The configuration details of chopping node 110 are shown in FIGS. 3A and 3B. Chopping node 110 compares the feedback signal output by the feedback subsystem 150 with the response signal output by the sensor electrodes 105. Chopping node 110 outputs an error signal based on the difference between the feedback signal from the feedback subsystem 150 and the response signal from the sensor electrodes 105.

The amplifier 115 amplifies the error signal output by the chopping node 110. The amplifier 115 may be any suitable amplifier. For example, the amplifier 115 may be a low noise chopped amplifier. Configuration details of amplifier 115 are shown in more detail in FIGS. 3A and 3B. The amplifier 115 may also be part of the control system 120. For example, the control system 120 may comprise a loop filter that includes one or more integrators, and the amplifier 115 may be configured as an integrating amplifier, thereby acting as the first integrator in the control system 120. As shown in FIG. 1, an output terminal of the amplifier 115 is coupled to an input terminal of control subsystem 120.

The amplified error signal is output from amplifier 115 and is input to control subsystem 120. Control subsystem 120 may comprise a loop filter and/or a quantizer. For example, one common implementation of the signal recording system 100 may include a sigma-delta analog-to-digital converter. In this case, control subsystem 120 may comprise a loop filter that consists of one or more integrators as well as a quantizer such as a comparator or coarse analog-to-digital converter. Control subsystem 120 may generate, in some embodiments, the feedback signal and provide it to feedback actuator 130. Control subsystem 120 may receive, in some embodiments, the response signal from sensor electrodes 105 and/or the error signal from chopping amplifier circuit 140. In some embodiments, control subsystem 120 may calculate the response signal using the feedback signal and the amplified error signal that amplifier 115 outputs. In some embodiments, the response signal and the feedback signal may be transmitted directly to control subsystem 120. The control subsystem 120 may provide the feedback signal, response signal, and/or amplified error signal to recording subsystem 125. In some embodiments, for example in embodiments in which common mode impedance boosting is implemented, feedback system 150 may be divided into two portions where the first portion handles common mode and the second portion handles differential mode.

Recording subsystem 125 may be any recording device for receiving, processing, and storing information related to the neural recording session. For example, the recording subsystem 125 may comprise a microcontroller or digital signal processing system that receives signals from the feedback subsystem 150 and translates those signals into digital data that represent the voltage signal from the sensor electrodes 105. Recording subsystem 125 could also be a desktop or computer, a mobile phone, tablet, or other electronic device capable of receiving signals from the control subsystem 120 and translating those signals into representative digital data. The digital data can then be transmitted to an I/O device 135 in order to be viewed by a technician or other user. Alternatively or additionally, the digital data can be stored in a digital storage medium 145. Digital storage medium 145 may include a flash memory, a disk drive, a cloud database, and/or any other suitable digital storage medium. Recording subsystem 125 may provide information for each session for recording and storing into digital storage medium 145 and/or displaying on I/O device 135. In some embodiments, recording subsystem 125 may be incorporated into control subsystem 120 rather than being two separate subsystems. Information recorded by recording subsystem 125 for each neural recording session may be obtained by control subsystem 120 via I/O device 135 (which may also function as an input device), and such information may include patient data including name, age, and so forth. Information obtained during the neural recording session including the parameters of feedback signals, response signals, and/or amplified error signals in addition to any stimulation signals may also be provided by control subsystem 120 to recording subsystem 125 for recording in digital storage medium 145.

I/O device 135 may be any input and/or output device for providing information derived from the response signal, feedback signal, and/or amplified error signal to a technician or other user that is monitoring the patient response being analyzed by the neural recording system 100. The I/O device 135 may be, for example, a visual display. The visual display may provide the response signal, feedback signal, and/or amplified error signal information to the technician in, for example, a graphical and/or numerical format. The I/O device 135 may provide, in some embodiments, an audible output from, for example, a speaker. The I/O device 135 may receive the information from the recording subsystem 125 wirelessly or through a wired connection. I/O device 135 may further function as an input device to receive patient information including, for example, age, name, and so forth for the patient. The technician may also enter into the I/O device 135 parameters for the recording session, such as for example, length of session, stimulus information, and so forth.

Control subsystem 120 may include circuitry and/or a computer system that generates a feedback signal designed to substantially match the response signal from sensor electrodes 105. The feedback signal may substantially match the response signal but be of the opposite polarity such that the feedback signal may substantially cancel out the response signal. In this way, when the feedback signal is combined with the response signal, the error difference may be substantially zero. Control subsystem 120 may provide the feedback signal to feedback actuator 130. Control subsystem 120 may use the amplified error signal to tune the feedback signal to more closely match the response signal from the sensor electrodes 105 before applying the feedback signal via feedback actuator 130. As an example, the recording system 100 may include a sigma-delta modulator implemented with chopping node 110, amplifier 115, control subsystem 120, and feedback actuator 130. In one such example, control subsystem 120 may comprise an integrating amplifier and a single-bit quantizer, and feedback actuator 130 may comprise a single-bit digital-to-analog converter. When the amplified error signal from amplifier 115 is positive, the integrator's output may increase, and when the amplified error signal from amplifier 115 is negative, the integrator's output may decrease. The single-bit quantizer may output a digital one (1) when the integrator's output is positive, and it may output a digital zero (0) when the integrator's output is negative. This stream of ones and zeros may be transformed by the single-bit digital-to-analog converter of feedback actuator 130 into a voltage waveform which may toggle between a positive and negative reference voltage depending on the digital value from the quantizer. For example, the voltage waveform at the output of feedback actuator 130 may equal a positive reference voltage when the digital value is one (1) and may equal a negative reference voltage when the digital value is a zero (0). This toggling voltage waveform may be applied to the chopping node 110. If the feedback subsystem 150 is designed properly, the voltage signal applied to chopping node 110 by feedback actuator 130 will match the response signal in the frequency band of interest. For example, for neural signals, the band of interest may be ten Hertz (10 Hz) to one kiloHertz (1 kHz), and the feedback signal may be expected to match the response signal well in this band. In practice, there may be a small mismatch between the feedback signal and the response signal in this frequency band (10 Hz-1 kHz), and there may be a larger mismatch outside of this frequency band, so that a non-zero error signal may be generated by the chopping amplifier circuit 140. Other variations of control subsystem 120 may include higher-order loop filters, such as would be used in a higher order sigma-delta modulator. Such a loop filter may include multiple integrator or amplifier stages, and may be implemented with continuous time or discrete time circuit techniques. Control subsystem 120 may include a multi-bit quantizer like a flash analog-to-digital (ADC) converter or a successive approximation register ADC. Feedback actuator 130 may include different kinds of digital-to-analog converters (DACs), such as switched capacitor DAC, current DAC, voltage DAC, or resistor DAC. Feedback actuator 130 may also include single-bit or multi-bit implementations. Alternatively, control subsystem 120 and feedback actuator 130 may be implemented in a purely analog fashion. Such an implementation may include amplifiers and/or attenuators in place of quantizers and DACs.

FIG. 1 discloses an example signal recording system 100 to record neural signals from a subject (i.e., patient), however, the chopping amplifier circuit 140 may be used in any high precision electronic circuit for boosting the circuit input impedance. Further, the example signal recording system 100 may include more or fewer components without departing from the scope of this disclosure.

Figures 2A, 2B:
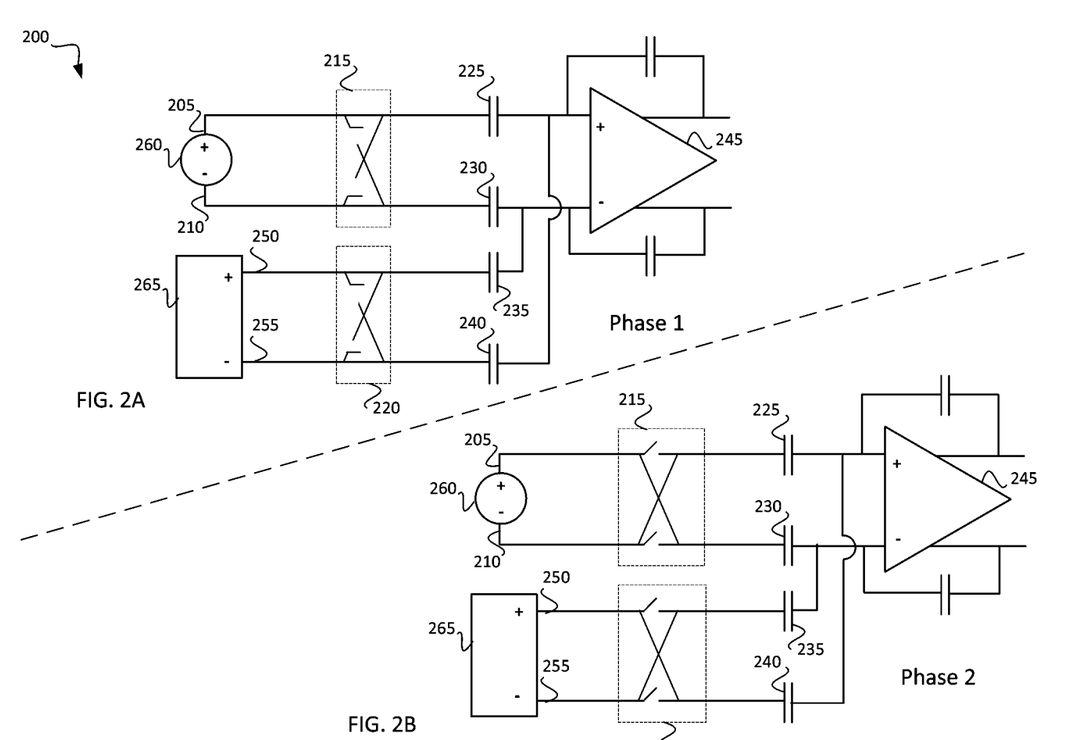
FIGS. 2A and 2B illustrate the two phases of a prior art front-end of a signal recording system having a chopping amplifier.

FIGS. 2A and 2B depict an example chopping amplifier 200 in each of the two phases. The configuration of chopping amplifier 200 produces an undesirable low input impedance as is described in more detail herein.

FIG. 3A illustrates a more detailed view of the chopping amplifier circuit 140 shown in FIG. 1. In this example, the chopping amplifier circuit 140 employs two different choppers 315 and 320. FIG. 3A shows the choppers 315 and 320 during phase 1, and FIG. 3B shows the choppers 315 and 320 during phase 2. The phases are described further herein. In both phases, the choppers 315 and 320 receive response signals from one or more sensor electrodes 105 and from feedback actuator 130. Unlike the configuration of chopping amplifier 200, one sensor electrode output terminal 305 (e.g., the positive output terminal) is coupled to a first input terminal of the first chopper 315, and a second sensor electrode output terminal 310 (e.g., the negative output terminal) is coupled to a first input terminal of the second chopper 320 in chopping amplifier circuit 140. Similarly, one feedback subsystem output terminal 345 (e.g., the positive output terminal) is coupled to a second input terminal of the first chopper 315, while a second feedback subsystem output terminal 350 (e.g., the negative output terminal) is coupled to a second input terminal of the second chopper 320. In contrast, a chopping amplifier configuration having low input impedance may have both sensor electrode output terminals 305 and 310 coupled to one chopper 315 and both feedback subsystem output terminals 345 and 350 coupled to the second chopper 320. Accordingly, in chopping amplifier circuits, such as chopping amplifier 200 as shown in FIGS. 2A and 2B, the second (e.g., negative) sensor electrode output terminal 210 is coupled to the second input terminal of the first chopper 215, and the first (e.g., positive) feedback subsystem output terminal 250 is coupled to the first input terminal of the second chopper 220. In the improved configuration depicted in FIGS. 3A and 3B, the cross-coupling such that an input of each chopper 315 and 320 are coupled to the sensor electrodes 105 and another input of each chopper 315 and 320 are coupled to the feedback subsystem 150, substantial benefits are obtained. By cross-coupling both of the sensor electrode outputs 305 and 310 and the feedback subsystem outputs 345 and 350 with the first chopper 315 and the second chopper 320, input impedance of the circuit is boosted. The higher input impedance offers benefits including an expanded frequency range of detectable signals from the sensor electrodes 105, protection of the patient's tissue near the sensor electrodes 105, and capacitors used to couple from the sensor electrodes to the chopping amplifier circuit can be smaller.

The first chopper 315 and the second chopper 320 are used to reduce noise and offset in the circuit as described in more detail below. The first output terminal of the first chopper 315 is coupled to a capacitor 325, which is coupled to a first (e.g., positive) input terminal of the amplifier 115. The second output terminal of the first chopper 315 is coupled to a capacitor 335, which is coupled to the second (e.g., negative) input terminal of the amplifier 115. The first output terminal of the second chopper 320 is coupled to a capacitor 330 that is also coupled to the second input terminal of amplifier 115. Capacitors 325 and 330 are a capacitor pair that are each the same size. Further the second output terminal of the second chopper 320 is coupled to a capacitor 340 that is also coupled to the first input terminal of the amplifier 115. At the first (e.g., positive) input terminal 355 of amplifier 115, the voltage on capacitor 325 combines with the voltage on capacitor 340. As described in more detail herein, the combined voltages on capacitors 325 and 340 substantially cancel each other out, leaving a first error difference between the output signal of sensor electrodes 105 and feedback subsystem 150. At the second (e.g., negative) input terminal 360 of amplifier 115, the voltage on capacitor 330 combines with the voltage on capacitor 335. The combined voltages on capacitors 330 and 335 also substantially cancel each other out, leaving a second error difference between the output signal of feedback subsystem 150 and sensor electrodes 105.

In some embodiments, capacitors 325, 330, 335, 340 are not each a single capacitor but are instead capacitor arrays. For example, the capacitor arrays can have two or more capacitors and the voltage out of feedback subsystem output 345 can be divided into several voltages each controlling one of the capacitors of the capacitor array of capacitor 335 and the voltage out of feedback subsystem output 350 can be divided into several voltages each controlling one of the capacitors of the capacitor array of capacitor 340. The same principles can be applied in examples where capacitors 325 and 330 include capacitor arrays. In this way the output of the feedback signal can be split to more accurately create the matching signal for the sensor output.

The amplifier 115 receives the two error differences and amplifies the difference between the first error difference and the second error difference. The amplified error difference is transmitted to control subsystem 120. Feedback capacitors 365 and 370 provide feedback from the output terminal of amplifier 115 to the input terminals 355 and 360 of amplifier 115 to stabilize the amplifier 115. The amplifier 115 shown in FIGS. 3A and 3B has two output terminals, indicating a differential output. In such an amplifier, the relevant output signal from the amplifier 115 is the difference between the signals from the two output terminals. In some embodiments, amplifier 115 may have a single output terminal. The output terminal (e.g., either the single output terminal or the two depicted output terminals that generate a differential output) are electrically coupled to the control subsystem 120 as depicted in FIG. 1.

During operation, the choppers 315 and 320 switch between two phases based on the configuration of the switches incorporated into each chopper 315, 320. As seen in FIG. 3A, in the first phase, the cross-overs of the choppers 315 and 320 are open and the straight-line connections are closed. As shown in FIG. 3B, in the second phase, the cross-overs of the choppers 315 and 320 are closed and the straight-line connections are open. This causes the choppers 315 and 320 to alternate between a straight-line connection and a cross-over connection. The choppers 315 and 320 switch at a predetermined frequency between the first phase and the second phase. Amplifiers like the amplifier 115 generally have a higher noise density at low frequencies in comparison to at high frequencies. Neural signals and other response signals that may be recorded by a recording system 100 are also typically at low frequencies, inside the frequency band where the amplifier 115 noise is high. The chopping of choppers 315 and 320 is used to avoid the overlap between the high noise of the amplifier 115 and the signal of interest at low frequencies. Chopping modulates the response signal from low frequencies up to the chopping frequency, which can be chosen to be above the frequency band where the noise density of the amplifier 115 is high. Another set of choppers later in the signal path (e.g., inside control subsystem 120) then demodulate the signal back to its original frequency band while modulating the noise and offset of the amplifier 115 up to the chopping frequency where it can be filtered out by filters in the control subsystem 120 or recording subsystem 125.

With respect to the sensor electrode output terminals 305 and 310, during the first phase, the first (e.g., positive) electrode output terminal 305 is coupled to capacitor 325, and the output terminal of capacitor 325 is coupled to the first input terminal 355 of the amplifier 115. The second (e.g., negative) electrode output terminal 310, during the first phase, is coupled to capacitor 330, and the output terminal of capacitor 330 is coupled to the second input terminal of amplifier 115.

With respect to the feedback subsystem output terminals 345 and 350, during the first phase, the first (e.g., positive) feedback subsystem output terminal 345 is coupled to capacitor 335. The output terminal of capacitor 335 is coupled to the second input terminal 360 of the amplifier 115. The second (e.g., negative) feedback subsystem output terminal 350, during the first phase, is coupled to capacitor 340, and the output terminal of capacitor 340 is coupled to the first input terminal 355 of amplifier 115.

Accordingly, assigning a value of VER to the first sensor electrode output 305 and −VER to the second sensor electrode output 310, during the first phase, capacitor 325 sees a value of VER and capacitor 330 sees a value of −VER. Assigning a value of VMC to the first feedback subsystem output 345 and −VMC to the second feedback subsystem output 350, during the first phase, capacitor 335 sees a value of VMC and capacitor 340 sees a value of −VMC. The voltages on capacitors 325 and 340 are combined at the first input terminal 355 of amplifier 115 to a VIN+ value of [VIN+=VER+−VMC]. In a properly working chopping amplifier circuit 140, VER and VMC should be substantially the same voltage value. This is in part because the signal recording system uses the amplified error difference output by amplifier 115 as feedback to correct or tune the feedback signal from feedback subsystem 150. Therefore, VER substantially equals VMC, so the voltage input VIN+ to amplifier 115 at first input terminal 355 is substantially zero, but because in practice VER will not exactly match VMC, an error difference between VER and VMC will be the input voltage VIN+ to the first input terminal 355 of amplifier 115. Similarly, the voltages on capacitors 330 and 335 are combined at the second (e.g., negative) input terminal 360 of amplifier 115 to a VIN− value of [VIN−=−VER+VMC]. Again, because VER substantially equals VMC, the voltage input VIN− to amplifier 115 at second input terminal 360 is substantially zero, but because in practice VER will not exactly match VMC, an error difference between VER and VMC will be the input voltage VIN− to the second input terminal 360 of amplifier 115. The difference between the error differences VIN+ and VIN− are amplified by amplifier 115, which outputs the amplified error difference to the control subsystem 120.

As described above, the capacitors 325, 330, 335, and 340 each have the same capacitance value. However, in some embodiments the capacitors 325, 330, 335, and 340 may not have the same value. For example, capacitors 325 and 330, which form a capacitor pair, may not be equal to capacitors 335 and 340, which form a second capacitor pair. In the capacitor pair 325 and 330, the capacitor 325 and the capacitor 330 have the same value. Similarly, in the capacitor pair 335 and 340, the capacitor 335 and the capacitor 340 have the same value. In some embodiments, capacitor 335 is a capacitor array and capacitor 340 is a capacitor array, as described above, and the arrays 335 and 340 have the same total value. Similarly, capacitors 325 and 330 may be implemented as capacitor arrays in some examples. As such, the capacitors in each capacitor pair are equal in size and opposite in polarity. When the first and second capacitor pairs have different values, the charge coming out of the capacitors is still intended to be equal to boost the impedance. In that case, VER will not match VMC since the capacitor values do not match and this will ensure that the charge coming out of the capacitors 325, 330, 335, and 340 are substantially equal as dictated by feedback system 150. In those cases, the first feedback subsystem output terminal 345 and second feedback subsystem output terminal 350 have values that ensure the charge coming from capacitor 335 matches that of capacitor 330 and the charge coming from capacitor 340 matches that of capacitor 325. Note that even if a capacitor array is used rather than a single capacitor, the total charge from the capacitor array can be used to determine the charge.

FIG. 3B illustrates the chopping amplifier circuit 140 during the second phase of the choppers 315 and 320. During the second phase, the first sensor electrode output terminal 305 is coupled to capacitor 335. The second sensor electrode output terminal 310, during the second phase, is coupled to capacitor 340. The first feedback subsystem output terminal 345 is coupled to capacitor 325, and the second feedback subsystem output terminal 350 is coupled to capacitor 330 during the second phase. The second phase, in other words, switches each of the choppers 315 and 320.

Using the above assigned values of VER to the first electrode output 305, −VER to the second electrode output 310, VMC to the first feedback subsystem output 345, and −VMC to the second feedback subsystem output 350, during the second phase, capacitor 325 sees a value of VMC, capacitor 330 sees a value of −VMC, capacitor 335 sees a value of VER, and capacitor 340 sees a value of −VER. Therefore, the input to first input terminal 355 of amplifier 115 during phase 2 is [VIN+=VMC+−VER], and the input to second input terminal 360 of amplifier 115 during phase 2 is VIN−=VER+−VMC]. Note that the amplifier 115 may account for offset because, as the choppers switch, the input to each amplifier input alternates between positive and negative, allowing identification of the error difference as well as identification of any offset.

Again, in a properly working feedback system, VER and VMC should be substantially the same voltage value. Therefore, during phase two, and assuming the feedback has properly adjusted the feedback subsystem output, the values at each capacitor 325, 330, 335, and 340 are substantially the same as during phase 1. See Table 1.

TABLE 1

| Chopping Amplifier Circuit | Phase 1 | Phase 2 |
| --- | --- | --- |
| Capacitor 325 | $V_{ER}$ | $V_{MC}$ |
| Capacitor 330 | $-V_{ER}$ | $-V_{MC}$ |
| Capacitor 335 | $V_{MC}$ | $V_{ER}$ |
| Capacitor 340 | $-V_{MC}$ | $-V_{ER}$ |

When the feedback signal from the feedback subsystem 150 closely matches the response signals from the sensor electrode 105, the capacitor 325, 330, 335, and 340 voltage values do not change substantially. Accordingly, at each switch of the chopping phases, no input voltage (or only a very small input voltage if there is error between VER and VMC) is needed to charge the capacitors 325, 330, 335, and 340. The configuration of chopping amplifier circuit 140, therefore, boosts input impedance over chopping amplifiers like chopping amplifier 200 because there is no requirement to charge the capacitors at each phase using the source as will be shown in more detail below.

The described behavior of the chopping amplifier circuit 140 is distinctly different from chopping amplifier configurations having low input impedance like chopping amplifier 200. FIGS. 2A and 2B show chopping amplifier 200 having a configuration that results in low input impedance as compared to chopping amplifier 140. The configuration of chopping amplifier 200 does not include the cross-coupling of the sensor electrodes 105 and feedback subsystem 265 with the first chopper 215 and second chopper 220. Accordingly, the choppers reduce noise and offset in the circuit, but the chopping circuit 200 suffers from low input impedance due to the configuration.

As shown in example chopping amplifier 200, first (e.g., positive) electrode output terminal 205 from sensor electrodes 260 is coupled to the first input for the first chopper 215, and second (e.g., negative) electrode output terminal 210 is coupled to the second input for the first chopper 215. The first output terminal of the first chopper 215 is coupled to the first capacitor 225, which is input to the first (e.g., positive) input terminal of amplifier 245. The second output terminal of the first chopper 215 is coupled to the second capacitor 230, which is input to the second (e.g., negative) input terminal of amplifier 245. Therefore, during the first phase, the first sensor electrode output terminal 205 is coupled to capacitor 225, and the second sensor electrode output terminal 210 is coupled to capacitor 230.

During the second phase, first sensor electrode output terminal 205 is coupled to capacitor 230, and second sensor electrode output terminal 210 is coupled to capacitor 225. Further, the first feedback subsystem output terminal 250 is coupled to the first input for the second chopper 220, and the second (e.g., negative) feedback subsystem output terminal 255 is coupled to the second input for the second chopper 220. Therefore, during the first phase, the first feedback subsystem output terminal 250 is coupled to capacitor 235, which is input to the second input terminal of amplifier 245. The second feedback subsystem output terminal 255, during the first phase, is coupled to capacitor 240, which is input to the first input terminal of amplifier 245. During the second phase, the first feedback subsystem output terminal 250 is coupled to capacitor 240, and the second feedback subsystem output terminal 255 is coupled to capacitor 235.

Assigning a value of VER to the first electrode output 205 and −VER to the second electrode output 210, during the first phase, capacitor 225 sees a value of VER and capacitor 230 sees a value of −VER. Assigning a value of VMC to the first feedback subsystem output 250 and −VMC to the second feedback subsystem output 255, during the first phase, capacitor 235 sees a value of VMC and capacitor 240 sees a value of −VMC. During the second phase, the voltage values at each capacitor 225, 230, 235, and 240 are substantially opposite of the voltage values during the first phase. See Table 2.

TABLE 2

| Prior Systems | Phase 1 | Phase 2 |
| --- | --- | --- |
| Capacitor 225 | $V_{ER}$ | $-V_{ER}$ |
| Capacitor 230 | $-V_{ER}$ | $V_{ER}$ |
| Capacitor 235 | $V_{MC}$ | $-V_{MC}$ |
| Capacitor 240 | $-V_{MC}$ | $V_{MC}$ |

Because each capacitor voltage value changes from positive to negative at each phase change in this configuration, a charge is required from the input to switch each capacitor 225, 230, 235, and 240 on each phase. The capacitors 225 and 230 are charged by sensor electrodes 260 and capacitors 235 and 240 are charged by feedback subsystem 265. This charge happens at each phase change. The phases switch at a frequency, which can be any frequency (e.g., 100 Hertz) appropriate for the circuit. The required charge from the electrode source 260 lowers the input impedance of the circuit. As the frequency of the switching increases, the input impedance of the circuit decreases. Further, the lower the input impedance, the smaller the frequency range of detectable signals from the electrode output. This occurs because any capacitors that couple the sensor electrodes to the chopping circuit may create a high pass corner when combined with the input resistance of the circuit. The value of the capacitors that couple the sensor electrodes to the chopping circuit multiplied by the input impedance of the circuit equals a time constant that is ideally large to make the time as long as possible, making the lower frequency threshold as low as possible. For example, in order for the recording system to measure signals at frequencies down to one Hertz (1 Hz), a time constant on the order of one (1) second or more may be desirable. If capacitors with value of one hundred nanofarad (100 nF) are used to couple the signal from the interface to the choppers, then an input impedance greater than ten megaohm (10 mΩ) may be desirable in order to pass signals at one Hertz (1 Hz). However in the configuration depicted in FIGS. 2A and 2B, the time constant may be small (e.g., much less than one second) because the input impedance is low (e.g., much less than ten megaohm). Therefore, lower frequency output signals from the electrodes may not be detected because they are filtered out at the high pass corner.

Note that the input to the amplifier 245 is the error difference between the sensor electrodes 260 and the feedback subsystem 265. The amplifier 245 amplifies the difference between the error differences. During the first phase, the error difference at the first input terminal is [VIN+ =VER+−VMC], and the error difference at the second input terminal is [VIN−=VMC+−VER]. During the second phase, the error difference at the first input terminal is [VIN+ =VMC+−VER], and the error difference at the second input terminal is [VIN−=VER+−VMC]. Therefore, the amplifier may amplify the error difference between the two sources and account for any offset. This is because as the choppers switch, the input to each amplifier input alternates between positive and negative, allowing identification of the error difference as well as identification of any offset. The prior art chopping amplifier circuit 200 shown in FIGS. 2A and 2B reduces noise and offset in the circuit, and the output of amplifier 245 is similar to the output of amplifier 115 described in FIGS. 3A and 3B. However, the undesirable effect of lowered input impedance can be remedied with the chopping amplifier circuit 140 described in FIGS. 3A and 3B.

Returning to the chopping amplifier circuit 140 of FIGS. 3A and 3B, any small charge needed for capacitors 325, 330, 335, and/or 340 may come from the feedback actuator 130 of the feedback subsystem 150 rather than the sensor electrodes 105 because the feedback actuator 130 is coupled to at least one capacitor of each pair coupled to one of the choppers 315 and 320. The input impedance of the circuit is boosted as compared to chopping amplifier 200 because the capacitors 325, 330, 335, and 340 do not need to be charged or only charged a very small amount. Further, by increasing the input impedance of the circuit, lower electrode response signal frequencies are detectable, subject tissue is protected, and capacitors can be smaller. The lower electrode response signal frequencies are detectable because the high pass corner created by the coupling capacitors 375 and 380 between the sensor electrodes and the chopping circuit when combined with the input resistance of the circuit has a lower corner due to the higher input impedance as compared with that of chopping amplifier 200. Coupling capacitors 375 and 380 are optional within circuit 140. However, as discussed above, the coupling capacitor 375 and 380 value multiplied by the input impedance equals a time constant. The desired time constant is large to increase the frequency range of detectable signals. As the input impedance increases, the time constant increases (i.e., gets longer) and therefore lower frequencies are detectable because the high pass corner does not filter them out. Further, as the input impedance increases, smaller coupling capacitors 375 and 380 may be used while maintaining a reasonable high pass corner. The smaller coupling capacitors 375 and 380 may be desirable to limit the size of the device, which in some cases may be implanted into the subject (i.e., patient). Finally, a higher input impedance can protect the subject's tissue from damage. A circuit having a lower input impedance than the output impedance of the source may attempt to draw power (current and/or voltage) from the source. Therefore, a high input impedance can ensure that the chopping amplifier circuit 140 does not attempt to draw current from the sensor electrodes 105, which may damage the tissue of the patient.

It should further be appreciated that the input to the first terminal 355 of the amplifier 115 is from capacitor 325 and capacitor 340. During the first phase, the error difference between the first (e.g., positive) electrode output 305 (e.g., VER) and the second feedback subsystem output 350 (e.g., −VMC) are then the input to the first terminal 355 of the amplifier 115 (i.e., VIN+=VER+−VMC). Note that this value is the same as the input to the first terminal of amplifier 245 of FIG. 2A (i.e., during phase 1). However, during the second phase, the error difference between the first (e.g., positive) feedback subsystem output 345 (VMC) and the second (e.g., negative) electrode output 310 (−VER) are then the input to the first terminal 355 of the amplifier 115 (i.e., VIN+=VMC+−VER). Note that this value is the same as the input to the first terminal of amplifier 245 of FIG. 2B (i.e., during phase 2). Further, the input to the second terminal 360 of amplifier 115 is from capacitors 330 and 335. During the first phase, the error difference between the first feedback subsystem output 345 (VMC) and the second electrode output 310 (−VER) are the input to the second terminal 360 of the amplifier 115 (i.e., VIN+=VMC+−VER). Note that this value is the same as the input to the second terminal of amplifier 245 of FIG. 2A (i.e., during phase 2). During the second phase, the error difference between the first electrode output 305 (VER) and the second (e.g., negative) feedback subsystem output 350 (−VMC) are input into the second terminal 360 of the amplifier 115 (i.e., VIN−=VER+−VMC). Again, the values input to the second terminal 360 in each phase are the same as those input to the second terminal of amplifier 245. Amplifier 115 then behaves as amplifier 245 was described to also output the amplified error signal. Accordingly, when VER and VMC are substantially similar, the error is substantially zero for each input terminal 355 and 360 at each phase. The alternating of the error calculation at each phase due to the switching allows for identification of the error between the two signals as well as identification of any offset value. The result is that, in addition to providing noise and offset reduction, this example chopping amplifier circuit 140 adds the benefit of boosting input impedance, which protects the subject's tissue, allows for expanded detection of lower frequency response signals, and provides the ability to use smaller capacitors.

Figure 4:
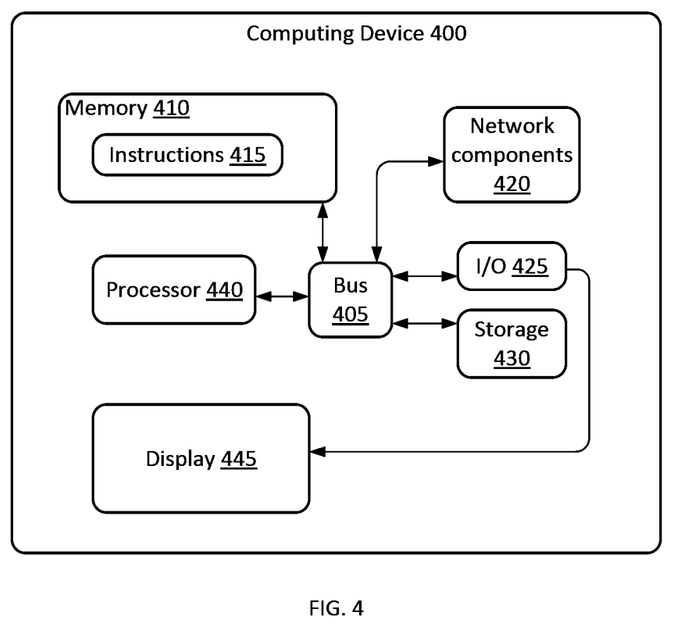
FIG. 4 illustrates an exemplary computer system.

FIG. 4 illustrates a block diagram of an example computer system 400. Computer system 400 can be any of the described computers herein including, for example, control subsystem 120. The computing device 400 can be or include, for example, a laptop computer, desktop computer, tablet, e-reader, smart phone or mobile device, smart watch, personal data assistant (PDA), or other electronic device.

The computing device 400 can include a processor 440 interfaced with other hardware via a bus 405. A memory 410, which can include any suitable tangible (and non-transitory) computer readable medium, such as RAM, ROM, EEPROM, or the like, can embody program components (e.g., instructions 415) that configure operation of the computing device 400. In some examples, the computing device 400 can include input/output ("I/O") interface components 425 (e.g., for interfacing with a display 445, keyboard, or mouse) and additional storage 430.

The computing device 400 can include network components 420. Network components 420 can represent one or more of any components that facilitate a network connection. In some examples, the network components 420 can facilitate a wireless connection and include wireless interfaces such as IEEE 802.11, Bluetooth, or radio interfaces for accessing cellular telephone networks (e.g., a transceiver/antenna for accessing CDMA, GSM, UMTS, or other mobile communications network). In other examples, the network components 420 can be wired and can include interfaces such as Ethernet, USB, or IEEE 1394.

Although FIG. 4 depicts a single computing device 400 with a single processor 440, the system can include any number of computing devices 400 and any number of processors 440. For example, multiple computing devices 400 or multiple processors 440 can be distributed over a wired or wireless network (e.g., a Wide Area Network, Local Area Network, or the Internet). The multiple computing devices 400 or multiple processors 440 can perform any of the steps of the present disclosure individually or in coordination with one another.

FIG. 5 illustrates another example of a more detailed view of the chopping amplifier circuit 140 shown in FIG. 1. In this embodiment, the common mode of the sensor electrode signal in addition to the differential mode of the sensor electrode signal is used to boost the full impedance (i.e., common mode and differential mode). The chopping amplifier circuit 140 in FIG. 5 is similar to that shown in FIG. 3A (only phase 1 of the circuit) with the addition of common mode sensing circuit 505. In this embodiment, common mode sensing circuit 505 receives the signal from the sensor electrode output terminals 305 and 310 and determines the common mode component of the signal from the sensing electrode 105. This common mode portion of the signal is output as common mode signal 510. The common mode signal 510 is added to the feedback output signal 345 and 350 with summing circuits 515 and 520. By adding the common mode signal 510 to the feedback subsystem output 345, which only outputs the differential matching signal, the full (common mode and differential mode) impedance is boosted.

Alternative embodiments may also include that differential mode is separately handled by a second set of capacitors 325, 330, 335, and 340. In some embodiments, common mode impedance may be boosted by providing common mode signal 510 to two additional capacitors (not shown) that are charged to the common mode signal value and one of each of the two additional capacitors is connected to each one of capacitors 325 and 330 via a switch (not shown) that closes to charge capacitors 325 and 330 to the common mode voltage during the transition between phase 1 and phase 2 of the circuit as shown in FIGS. 3A and 3B. Charging the capacitors 325 and 330 to the common mode signal between phases ensures no additional charge is needed to charge the capacitors 325 and 330, boosting the common mode impedance of the circuit. Additionally, two sets of differential capacitors (not shown) can be used to alternately provide the common mode charge where one set that was pre-charged to the common mode signal is connected to the capacitors 325 and 330 in one phase while the other set is being pre-charged to the common mode signal. Then in the following phase the second set (already charged with the common mode signal) is connected to the capacitors 325 and 330 while the first set is now being charged to the common mode signal. Additionally, in some embodiments, a second feedback subsystem 150 may be included such that one handles the differential mode impedance boosting and the other handles the common mode impedance boosting.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

Different arrangements of the components depicted in the drawings or described above, as well as components and steps not shown or described are possible. Similarly, some features and sub-combinations are useful and may be employed without reference to other features and sub-combinations. Embodiments of the present disclosure have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the present disclosure, a single component may be replaced by multiple components, and multiple components may be replaced by a single component, to provide an element or structure or to perform a given function or functions. Except where such substitution would not be operative to practice certain embodiments of the present disclosure, such substitution is considered within the scope of the present disclosure.

It is to be understood that the figures and descriptions of embodiments of the present disclosure have been simplified to illustrate elements that are relevant for a clear understanding of the present disclosure. Those of ordinary skill in the art will recognize, however, that these and other elements may be desirable. However, because such elements are well known in the art, and because they do not facilitate a better understanding of the present disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the present disclosure, a single component may be replaced by multiple components, and multiple components may be replaced by a single component, to provide an element or structure or to perform a given function or functions. Except where such substitution would not be operative to practice certain embodiments of the present disclosure, such substitution is considered within the scope of the present disclosure. A recitation of "a", "an" or "the" is intended to mean "one or more" unless specifically indicated to the contrary.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

The examples presented herein are intended to illustrate potential and specific implementations of the present disclosure. It can be appreciated that the examples are intended primarily for purposes of illustration of the present disclosure for those skilled in the art. There may be variations to these diagrams or the operations described herein without departing from the spirit of the present disclosure. For instance, in certain cases, method steps or operations may be performed or executed in differing order, or operations may be added, deleted or modified.

Furthermore, whereas particular embodiments of the present disclosure have been described herein for the purpose of illustrating the present disclosure and not for the purpose of limiting the same, it will be appreciated by those of ordinary skill in the art that numerous variations of the details, materials and arrangement of elements, steps, structures, and/or parts may be made within the principle and scope of the present disclosure without departing from the present disclosure as described in the claims.

That which is claimed is:

1. A front-end for a neural recording system, the front-end comprising:
    a sensor comprising first and second sensor output terminals;
    a feedback subsystem comprising first and second feedback output terminals;
    a first chopper comprising first and second input terminals, and first and second output terminals, wherein:
        the first input terminal of the first chopper is electrically coupled to the first sensor output terminal,
        the second input terminal of the first chopper is electrically coupled to the first feedback output terminal,
    a second chopper comprising first and second input terminals, and first and second output terminals, wherein:
        the first input terminal of the second chopper is configured to be electrically coupled to the second sensor output terminal,
        the second input terminal of the second chopper is configured to be electrically coupled to the second feedback output terminal;
    an amplifier comprising first and second amplifier input terminals;
    a first capacitor coupled to the first output terminal of the first chopper and the first amplifier input terminal;
    a second capacitor coupled to the second output terminal of the first chopper and the second amplifier input terminal;
    a third capacitor coupled to the first output terminal of the second chopper and the second amplifier input terminal; and
    a fourth capacitor coupled to the second output terminal of the second chopper and the first amplifier input terminal;
    wherein the first and second choppers are configured to operate in a first phase and a second phase, wherein:
    during the first phase:
        the first sensor output terminal, the second feedback output terminal, and the first and fourth capacitors are in electrical communication with the first amplifier input terminal, and
        the second sensor output terminal, the first feedback output terminal, and the second and third capacitors are in electrical communication with the second amplifier input terminal; and
    during the second phase:
        the first sensor output terminal, the second feedback output terminal, and the second and third capacitors are in electrical communication with the second amplifier input terminal, and the second sensor output terminal, the first feedback output terminal, and the first and fourth capacitors are in electrical communication with the first amplifier input terminal.

2. The front-end for the neural recording system of claim 1, further comprising:
a first coupling capacitor electrically coupled between the first input terminal of the first chopper and the first sensor output terminal; and
a second coupling capacitor electrically coupled between the first input terminal of the second chopper and the second sensor output terminal.

3. The front-end for the neural recording system of claim 1, wherein at least one of the first capacitor, the second capacitor, the third capacitor, or the fourth capacitor comprises a capacitor array.

4. The front-end for the neural recording system of claim 1, wherein the first capacitor and the third capacitor form a first capacitor pair, and the second capacitor and the fourth capacitor form a second capacitor pair, and wherein the first and third capacitors each have a first capacitance, the second and fourth capacitors each have a second capacitance, and wherein the first capacitance is different from the second capacitance.

5. The front-end for the neural recording system of claim 1, wherein the amplifier comprises at least one amplifier output terminal and wherein the at least one amplifier output terminal is electrically coupled to an input terminal of the feedback subsystem.

6. The front-end for the neural recording system of claim 1, wherein the sensor is configured to measure a response signal from a nerve of a patient.

7. The front-end for the neural recording system of claim 1, further comprising a common mode ("CM") sensing circuit having a CM output, and first and second summing circuits, wherein:
a first input of the first summing circuit is coupled to the first feedback output terminal;
a second input of the first summing circuit is coupled to the CM output; and
an output of the first summing circuit is coupled to the second input of the first chopper;
a first input of the second summing circuit is coupled to the second feedback output terminal;
a second input of the second summing circuit is coupled to the CM output; and
an output of the second summing circuit is coupled to the second input of the second chopper.

8. A method comprising:
providing the front-end for the neural recording system according to claim 1;
coupling the sensor to a patient; and
measuring a neural response of the patient using the front-end for the neural recording system.

9. The method of claim 8, wherein the front-end for the neural recording system further comprises:
a first coupling capacitor electrically coupled between the first input terminal of the first chopper and the first sensor output terminal; and
a second coupling capacitor electrically coupled between the first input terminal of the second chopper and the second sensor output terminal.

10. The method of claim 8, wherein at least one of the first capacitor, the second capacitor, the third capacitor, or the fourth capacitor comprises a capacitor array.

11. The method of claim 8, wherein the first capacitor and the third capacitor form a first capacitor pair, and the second capacitor and the fourth capacitor form a second capacitor pair, and wherein the first and third capacitors each have a first capacitance, the second and fourth capacitors each have a second capacitance, and wherein the first capacitance is different from the second capacitance.

12. The method of claim 8, wherein the amplifier comprises at least one amplifier output terminal and wherein the at least one amplifier output terminal is electrically coupled to an input terminal of the feedback subsystem.

13. The method of claim 8, wherein the sensor is configured to measure a response signal from a nerve of a patient.

14. The method of claim 8, wherein the front-end for the neural recording system further comprises a common mode ("CM") sensing circuit having a CM output, and first and second summing circuits, wherein:
a first input of the first summing circuit is coupled to the first feedback output terminal;
a second input of the first summing circuit is coupled to the CM output; and
an output of the first summing circuit is coupled to the second input of the first chopper;
a first input of the second summing circuit is coupled to the second feedback output terminal;
a second input of the second summing circuit is coupled to the CM output; and
an output of the second summing circuit is coupled to the second input of the second chopper.

* * * * *